United States Patent [19]

Schoendorfer et al.

[11] Patent Number: 4,911,833
[45] Date of Patent: * Mar. 27, 1990

[54] CLOSED HEMAPHERESIS SYSTEM AND METHOD

[75] Inventors: Donald W. Schoendorfer, Santa Ana, Calif.; William F. McLaughlin, 67 Balboa Coves, Newport Beach, Calif. 92663

[73] Assignee: William F. McLaughlin, Newport Beach, Calif.

[*] Notice: The portion of the term of this patent subsequent to Oct. 11, 2005 has been disclaimed.

[21] Appl. No.: 202,967

[22] Filed: Jun. 6, 1988

Related U.S. Application Data

[63] Continuation of Ser. No. 644,032, Aug. 24, 1984, Pat. No. 4,776,964.

[51] Int. Cl.$^4$ .............................................. B01D 21/26
[52] U.S. Cl. ................................ 210/167; 210/321.68; 210/782; 210/805
[58] Field of Search ................ 210/651, 782, 321.68, 210/805, 167, 195.2, 259, 434; 494/44, 65, 36, 84, 32, 60, 35, 63, 67, 70, 74, 80, 77, 78; 604/6

[56] References Cited

U.S. PATENT DOCUMENTS

| | | | |
|---|---|---|---|
| 3,022,937 | 2/1962 | Dega | 233/28 |
| 3,519,201 | 7/1970 | Eisel et al. | 233/46 |
| 3,655,123 | 4/1972 | Judson et al. | 233/21 |
| 3,955,755 | 5/1976 | Breillatt, Jr. et al. | 233/3 |
| 4,262,840 | 4/1981 | Gronert et al. | 233/1 R |
| 4,341,343 | 7/1982 | Beckman | 233/26 |
| 4,350,156 | 9/1982 | Malchesky et al. | 128/214 R |
| 4,530,691 | 7/1985 | Brown | 494/45 |
| 4,636,193 | 1/1987 | Cullis | 494/45 |
| 4,734,089 | 3/1988 | Cullis | 494/27 |
| 4,776,964 | 10/1988 | Schoendorfer et al. | 210/651 X |

*Primary Examiner*—Frank Spear
*Attorney, Agent, or Firm*—Paul C. Flattery; Bradford R. L. Price; Daniel D. Ryan

[57] ABSTRACT

A centrifugal separator system is provided for extracting lighter matter from a liquid suspension. The separator includes a housing having an axis, an inlet port, a lighter matter outlet port and a heavier matter outlet port spaced from the inlet port. A rotatable interior double shell rotor is disposed within the housing. The rotor includes outer and inner shells and defines a centrifugation gap therebetween. The rotor is spaced from the housing by a flow gap. The outer shell includes means providing communication between the centrifugation gap, the inlet port and the heavier outlet port. Means are provided in the double shell rotor for conducting lighter matter from the centrifugation gap to the lighter matter outlet port.

14 Claims, 5 Drawing Sheets

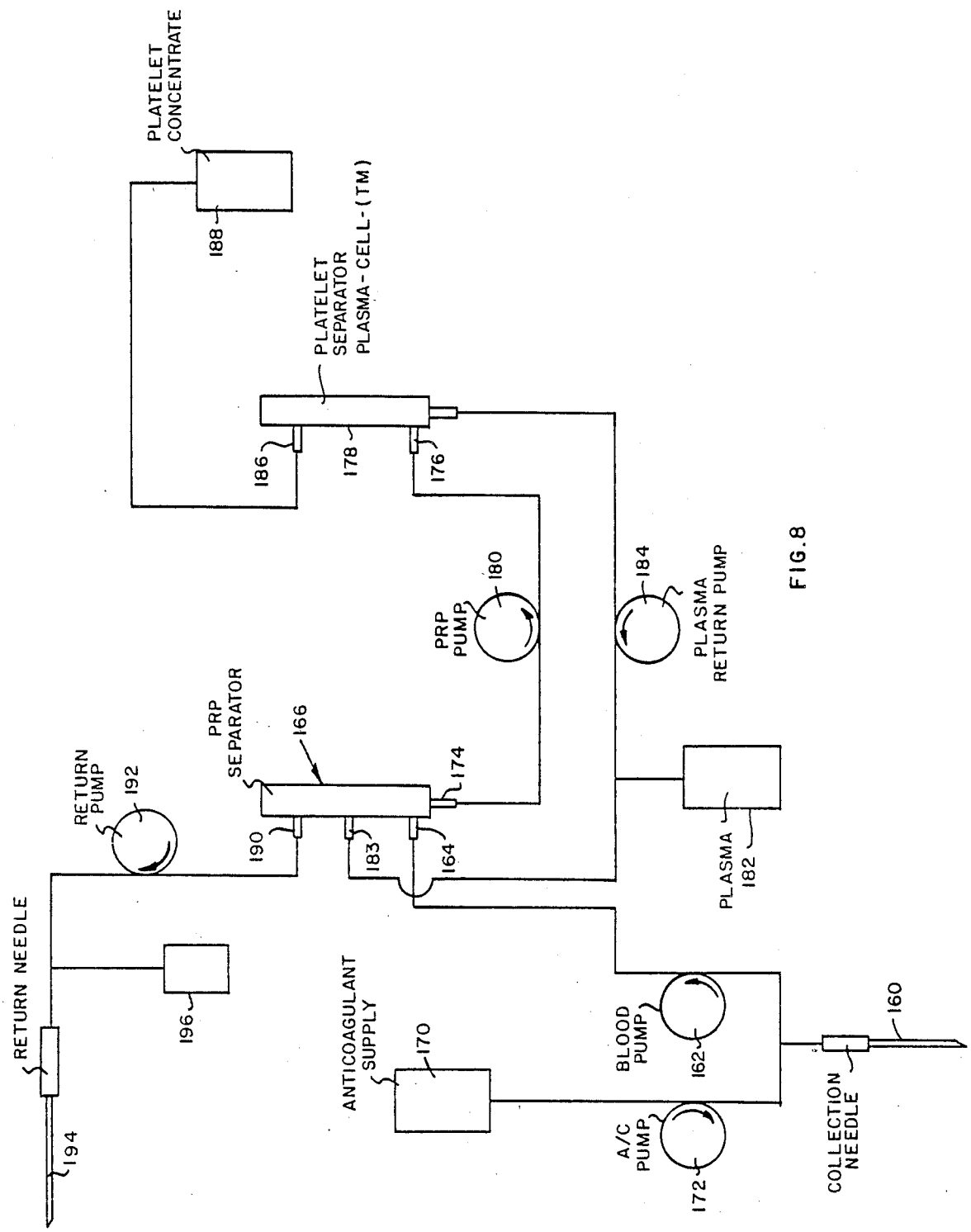

CLOSED HEMAPHERESIS SYSTEM AND METHOD

This is a continuation of U.S. patent application Ser. No. 06/644,032, filed on Aug. 24, 1984, now U.S. Pat. No. 4,776,964.

BACKGROUND OF THE INVENTION

This invention relates to the separation of one or more constituents of blood, and is more particularly directed to a closed system employing centrifugal force for separating different constituents from whole blood based on density or size, such as the separation of platelets and plasma from whole blood, ad to the method for carrying out such separation.

Whole blood consists broadly speaking of red blood cells, white blood cells, platelets and plasma. Hemapheresis, which is directed to the separation of one or more constituents of blood, encompasses the extraction of many different constituents in the present state of the art. Plasma, for example, is separated from whole blood taken from donors and stored, with the packed cell remainders from the blood being returned to the donors. Red blood cells are concentrated and stored or reused, sometimes being held in frozen state before reuse.

There are numerous therapeutic apheresis applications under study in which, using temporary or permanent separation of blood constituents, treatments or procedures are applied with sometimes dramatic benefit in amelioration of specific diseases or afflictions. It is sometimes desirable to separate leukocytes (white cells) from the red blood cells. In other instances it is sought to extract platelets, which have a principal role in the clotting function, from red blood cells, with or without plasma. In all of these applications, the fragile blood tissue must be handled in a non-traumatic manner to avoid the introduction of hemolysis or the initiation of the clotting action.

Hemapheresis has heretofore principally been carried out using centrifugation techniques, or membrane filtration systems. Spinning whole blood in a centrifuge at an appropriately high rate separates constituents in accordance with their density, and by using a sufficiently high rate and an adequately long period of time a fine discrimination in constituents, in accordance with density, can be achieved. Batch centrifugation, however, is cumbersome and lengthy and not suitable for many applications in which it is desired to extract more than one constituent or return packed cells or other constituents to a donor.

Accordingly, cell separators have been developed and are in use, such as the Model 30 offered by Haemonetics Corp. for cell extraction. This includes a disposable unit comprising a rotatable rotor with an interior core so configured that heavier matter moves to the outside diameter of the rotor/core combination, causing lighter matter to pass through interior ports to an outlet. To achieve appropriate centrifugation forces so as to separate materials that are quite close in density requires high speed operation, and this device must be run for a substantial period of time before separation occurs. The Haemonetics unit accordingly is driven at approximately 4800 rpm and is quite expensive (in the range of $45.00 per unit) for a disposable device. The great majority of such hemapheresis units are disposables that are used only once, because of the likelihood of transmission of infectious agents from one donor to another.

Furthermore the Haemonetics device is regarded as an open path configuration, in that the inlet and outlet paths for the constituents can communicate with the exterior environment through rotary seals. Microbe infiltration is a danger with such open systems, in consequence of which the FDA requires that the extracted matter be used within 24 hours to avoid the possibility of contamination.

Membrane filtration using a spinning rotor within a concentric shell has now been shown to be extremely effective for separating some constituents of blood from others, as for example separation of plasma from leukocytes, platelets and red blood cells. There is a substantial difference in density and in tee size of the elemental plasma which passes through the membrane relative to the cellular matter which is not filtered. However, when it is desired to separate certain cellular matter from other cellular matter, sizes may vary but little, as in the case with platelets which are of only slightly lower density in comparison to red blood cells. Membrane filtration does not appear to be appropriate for performing this function. Yet for certain applications it is of importance to extract platelets separately, and for others to provide a platelet rich plasma.

There is therefore a widespread need for a closed system and method that will separate different constituents of whole blood that are differentiable in density and size, but only in a minor degree, and to be able to do so with a relatively low cost disposable unit that is closed to the exterior environment. A further aim is to provide a closed system and method for the separation of platelet rich plasma from whole blood.

SUMMARY OF THE INVENTION

A hemapheresis system and method in accordance with the invention comprises a stationary housing that has an inner wall concentric about a central axis, and upper and lower ports communicating with the interior of the housing. Within the stationary housing is a double shell rotor concentrically mounted and rotatable about the central axis within the housing. The outer rotor wall has a predetermined close relationship to the stationary inner housing wall, permitting blood entering the housing cavity at its lower end to rise. However, blood also moves through the lower part of the rotor wall into a centrifugation gap defined by a substantially concentric inner wall or core, and advances upwardly while being subject to centrifugation action. The residence time and rotational rate are selected such that near the top of the rotor heavier cellular mater is concentrated at the outer radial region. From this upper region the heavier matter is withdrawn through orifices in the wall that communicate with the upper outlet port in the housing. Lighter matter moves upwardly over the top of he core to a central orifice which passes downwardly along the central axis to a conical outlet orifice. Means associated with the gap between the rotor and housing limit upward blood flow in this gap by creating a differential flow impedance, making the centrifugation gap the preferred passageway. The system thus continuously separates the majority of the input whole blood into the desired fractions.

This system is biologically closed inasmuch as flows into and out of the structure are made only through fixed ports and all rotary seals are internal to housing and completely isolated from the outside environment.

Using a rotor of approximately 4" in diameter, sufficient centrifugal force is generated for separation of matter such as platelets and plasma with a relatively low rotation rate of 2000 rpm or less. In addition the structure provides continuous centrifugal separation in a low cost, disposable unit.

Structures in accordance with the invention advantageously drive the rotor on sealed internal end bearings, at least a lower one of which has a central axial orifice to conduct plasma rich in a specific subpopulation of blood such as platelets from the center passageway in the rotor core to an outlet. A magnetic drive external to the housing couples to an internal magnetic element mounted on the upper part of the rotor so as to achieve the needed rotational velocity.

In one specific example of a system a differential flow impedance between the centrifugation gap and the rotor-housing gap is established by employing a bowl-shaped configuration in which blood follows a compound curvature path that expands radially outwardly in the mid region of the housing. In addition the rotor-housing gap leads to a closed upper end. Thus, whole blood fed into the bottom of the space between the rotor and housing moves through lower apertures in the rotor into the centrifugation gap and begins rotation with and upward movement within the rotor. Whole blood in the outer gap rises upwardly but being essentially stationary and acting against an enclosed volume reaches only a predetermined level determined by the pressure needed to advance blood to the top of the centrifugation gap. In the upper portion of the rotor, the heavier cellular matter separated by centrifugation encounters apertures in the outer perimeter of a top deflector plate, allowing packed cells to pass into an upper passage and out through an upper outlet port in the housing. Lighter matter, such as platelets and plasma, migrates inwardly next to the deflector plate until it reaches the central passageway in the rotor core and can move downwardly to the coaxial outlet orifice.

In a second example of a system in accordance with the invention, the inner wall of the housing and the rotor are substantially right circular cylinders. The differential flow impedance is provided by a mid region reduction in the gap between the rotor and inner housing wall, which may be augmented by injecting a compatible fluid such as plasma or saline solution into the narrow gap region. Here the heavier cellular matter may continuously egress the centrifugation gap at the top end of the rotor via holes in the circumference of the rotor wall to be mixed with the small amount of whole blood passing along the rotor-housing gap.

Another aspect of the invention is that a separator as described can be utilized in conjunction with membrane filtration in a closed system, to provide continuous extraction of packed cells and plasma for return to a donor, while separately dividing out platelets. In such a system, the centrifugal device of the invention feeds a platelet rich plasma to a membrane filtration unit, such as a device of the type having an interior sinner within a stationary housing. The outer wall of the spinner or the inner wall of the housing has a membrane covered surface and a conduit system for collecting plasma passing through the membrane. Consequently, by initial serial extraction of the platelet rich plasma from the whole blood and then removal of the plasma from the platelet rich mixture, one obtains the platelet concentration. As a variant on this system, a minor proportion of plasma is returned to the donor with packed cells by feeding a bypass plasma flow into the mid region of the cylindrical configuration of separator.

BRIEF DESCRIPTION OF THE DRAWINGS

A better understanding of the invention may be had by reference to the following description, taken in conjunction with the accompanying drawings, in which:

FIG. 8 is a block diagram representation of a system using the arrangement of FIGS. 5-7 for taking whole blood from a donor, returning certain fractions and collecting other certain fractions.

DETAILED DESCRIPTION OF THE INVENTION

Figure 1:
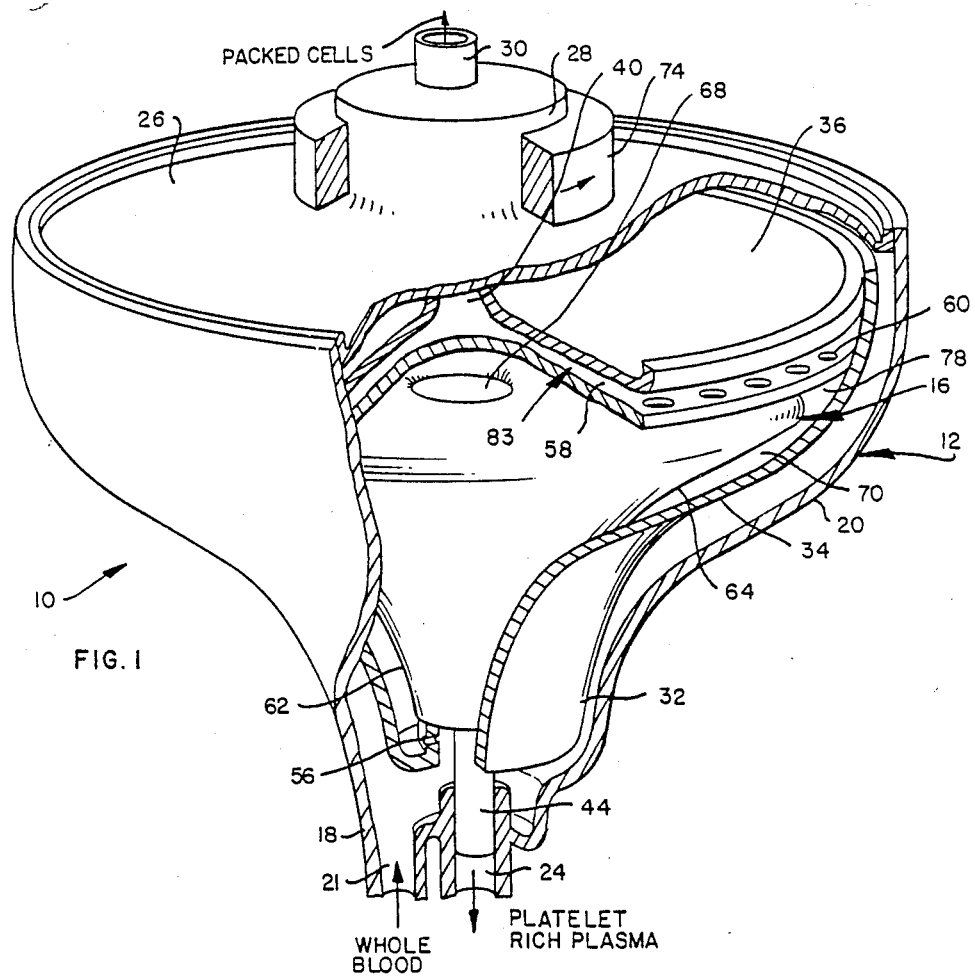
FIG. 1 is a perspective view, partially broken away, of a closed system for centrifugal separation of the constituents of blood.
Figure 2:
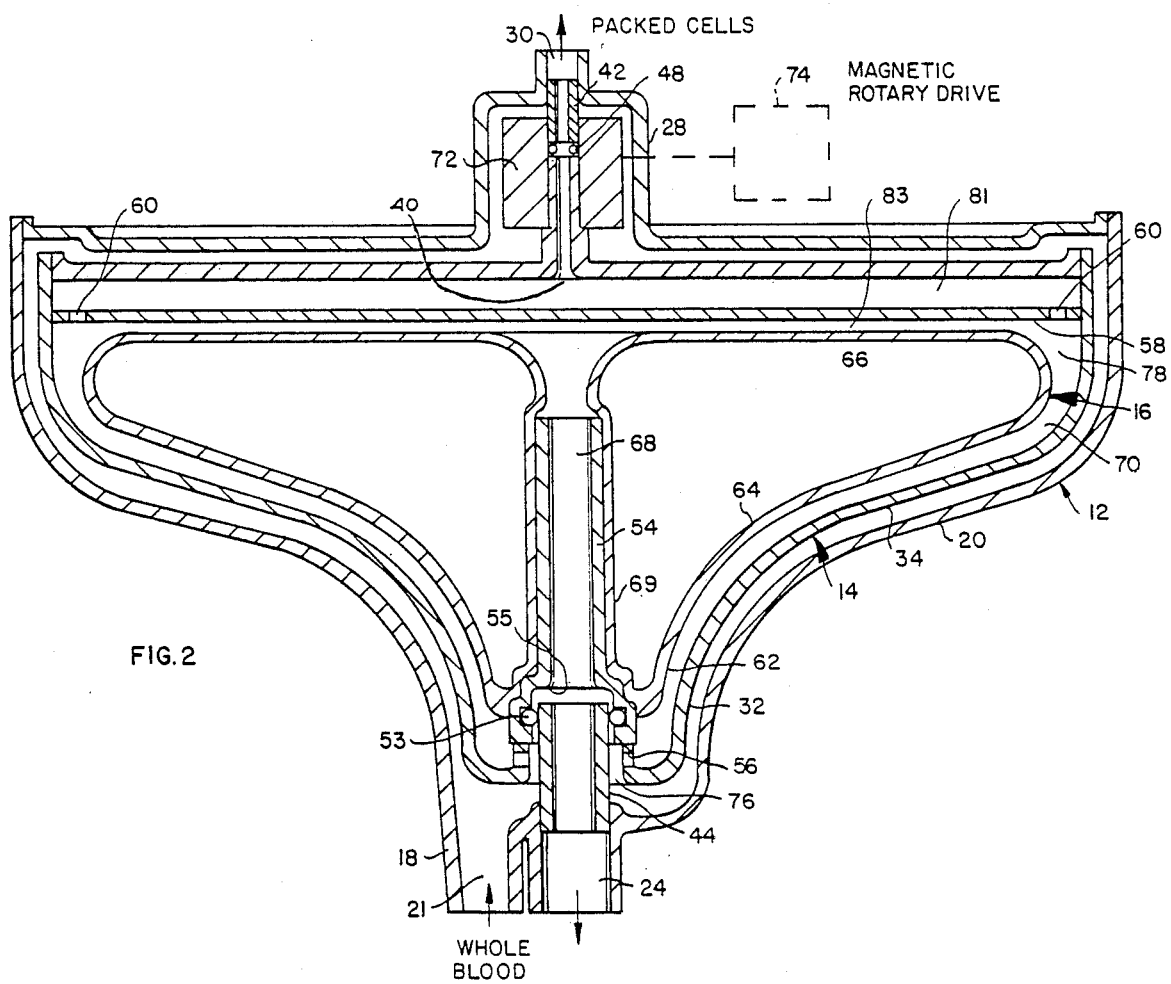
FIG. 2 is a cross-sectional view of the arrangement of FIG. 1.

A hemapheresis system in accordance with the invention, referring to FIGS. 1 and 2 of the drawings, comprises a biologically closed cell separator 10 including a stationary outer housing 12, a rotor outer wall 14, and a rotor core or inner wall 16 positioned within the rotor and defining with the rotor a double shell system. These elements are mounted concentric with a central vertical axis, the vertical disposition being referred to for convenience and ease of description in the specification and claims. It will be appreciated from the following description, however, that these systems do not require a particular orientation or gravitational effect and can be used in different juxtaposition than the true vertical. The space between the rotor wall 14 and core 16 defines a shaped centrifuging chamber that presents a lower impedance to flow than does the space between the rotor wall 14 and the housing 12. The housing 12 has a relatively narrow base portion 18 and an upwardly and outwardly diverging portion or bowl 20 which extends from the base to a final, substantially vertical section. The base portion 18 of the housing has an inlet port 21 and a lower central outlet port 24 positioned adjacent to each other along the central axis of the housing. The upper end of the housing is closed by an upper housing cap 26 connected across the end of the upwardly divergent bowl 20 of the housing. The housing cap 26 includes an upwardly extending boss at its mid region to form an upper central housing portion 28 which terminates in an upper outlet port 30 which also extends along and is coaxial with the central axis of the housing 12.

The rotor wall 14 has an exterior shape generally conforming to the periphery of the outer housing 12, and includes a lower, necked down, base portion 32 and an outwardly and upwardly curved portion 34 of double curvature forming a rotor bowl, the upper end of the rotor being closed on the outside by a horizontal rotor cap 36. The rotor wall 14 is spaced apart from the inner wall of the housing 12 to form an adequate clearance gap to receive a predetermined inlet volume of blood that is confined principally to the lower part of the space between the housing 23 and the rotor 14. Blood flowing upwardly in this space is substantially non-rotating because of the stationary housing 12 wall and in addition acts against gas trapped in the closed upper end of the rotor-housing gap, which gas acts as a compliance opposing increased upward advance of the inlet whole blood in this space. Thus in the rotor-housing gap the blood rises only to a certain level below the upper portion of the housing. The rotor cap 36 is formed with an upwardly extending central conduit 40 positioned along the central axis of the housing and the rotor, and communicating between the interior of the hollow rotor from the outer periphery of greatest diameter, and the upper outlet port 30 of the housing.

The rotor wall 14 is coupled to and is rotatable on upper and lower end bearings 42 and 44, respectively, that are coaxial with the central axis. The upper bearing 42 comprises a stationary stainless steel pivot pin having a central orifice and mounted as by a press fit in the upper outlet port 30 on the central housing portion 28. A compliant 0-ring 48 is captured between the rotatable central conduit 40 at the upper end of the rotor and the lower end of the pivot pin, to form an upper fluid and pressure seal between the rotor and the stationary housing. The lower bearing 44 comprises a stationary stainless steel pivot pin having a central orifice, fixed as by a press fit to the inner wall of the lower central outlet port 24. An 0-ring 52 is retained in a groove 53 formed on an upstanding central tubular portion 54 mounted on the base portion 32 of the rotor. The O-ring 52 makes slidable contact with the outer surface of the pivot in the orifice of the pin 44 and can shift slightly up and down the pivot pin in response to any limited axial motion of the rotor, and maintain a fluid and pressure seal between the rotor and the outer housing wall. Leakage across the seal can only take place within the interior of the housing so that the flow paths are isolated from exterior contamination. The lower end of the central tubular portion 54 has a shoulder 55 which contacts the upper end of pivot pin 44 to support the rotor wall 14.

The base of the central tubular member 54 on the rotor includes a plurality of apertures 56 spaced circumferentially around the member 54 about the pivot pin 44. The rotor 14 also includes an upper deflector plate 58 positioned just below the rotor cap 36, and connected across the upper end of the rotor in the region of greatest diameter thereof. The deflector plate 58 has a plurality of apertures 60 spaced circumferentially around the outer diameter of the plate near the outer periphery, and permitting flow into an upper chamber between the cap 36 and the deflector plate 58.

The rotor core 16 is mounted concentrically within the interior of the hollow rotor wall 14 to rotate as part of the rotor structure. The exterior configuration of the core 16 conforms to but is spaced apart from the rotor wall 14 so that the centrifugation volume has an increasing radii of curvature as one proceeds in the upward direction. The rate of change of the radius of curvature, however, is not constant. The core 16 comprises a base portion 62 and an upwardly and outwardly divergent portion 64 of bowl shape, a top portion 66 and a reentrant central conduit or passageway 68 connected to the base 62 and providing a flow path down from the top of the rotor. The central conduit 68 of the core includes a bottom portion 69 which is fitted around the central tubular portion 54 of the rotor 14 structure. The space between the outer wall of the core 16 and the rotor wall 14 therefore defines a second or centrifugation gap 70 through which the substantial majority of the volume of liquid to be processed is conducted.

A cylindrical magnet 72 is mounted within the upper central housing 28 concentrically about the central vertical axis, and is fixed as by press fitting around the central conduit 40 at the upper end of the rotor 14. The magnet 72 when driven thus turns the rotor and the interior core within the upper and lower end bearings 42 and 44. An external magnetic-type rotary drive, indicated only generally at 74, is disposed about the housing 28 to couple magnetically to the inner magnet 72 and provide synchronous rotation of the entire internal structure comprising the rotor wall 14 and core 16, without the requirement for any direct mechanical coupling.

The operation of the device of FIGS. 1 and 2 will be described hereafter in an application for the separation of whole blood into packed cells and platelet rich plasma. By packed cells is meant the combination of red blood cells and white blood cells, in the absence of platelets and plasma. It will be understood, however, that this is only one example of the application of the closed cell separator and method of the present invention, and other specific separation applications can be carried out utilizing the invention system.

Referring to FIGS. 1 and 2, the rotor 14 and core 16 are rotated by the external magnetic rotary drive 74, as whole blood enters within the stationary housing 12 through the whole blood inlet port 21. As the blood travels vertically upward into the housing interior it meets the bottom interior portion of the spinning rotor 14 and fills the gap 38 between the rotor and housing, rising to a predetermined height. This height is determined principally by the input pressure of the whole blood, the rotational velocity of the rotor, the relationship between the centrifugation gap and the relatively static rotor-housing gap, and the maximum radius of the centrifugation gap, and the level of back pressure presented by the gas entrapped above the blood, in the closed end of the rotor-housing space. The whole blood also enters and fills a gap 76 between the lower stainless steel pivot pin 44 and the base portion 32 at the interior of the tubular portion 54 of the rotor. The blood then passes through the ring of blood inlet apertures 56 into the lower end o the centrifugation gap 70 between the core 16 and the rotor wall 14. Blood in the gap 38 between the housing 12 and rotor wall 14 rotates only at the rotor surface through viscous drag and therefore establishes a hydraulic pressure source when the operation stabilizes.

The blood is forced upwardly within the centrifugation gap 70 via the apertures 56 by the initial centrifugal forces imparted by viscous drag from the spinning rotor, the input pressure, and also by the compensating hydraulic head generated by the blood level in the outer gap 38. As the system continuously feeds blood into the housing at the inlet port 22, the upward flow in the gap 70 between the core 16 and rotor wall 14 is continuous. As blood is impelled by centrifugal force and feed pressure, rotational velocity increases in the mid region where the radius arm of the centrifugation gap 70 increases. The outward surge of blood begins where the gap 70 turns outwardly, converting rotational energy of the rotor into upward movement which continues until the top portion of the rotor is reached. As previously noted, the rotor core 16 is designed to provide a low volume centrifugation gap 70 in the rotor, such as a volume of the order of about 50 ml.

As the whole blood moves upwardly from the inlet apertures 56 along the centrifugation gap 70 within the rotor, the less dense plasma portion containing platelets concurrently migrates toward the wall of the core 16 as the denser packed cells consisting of red and white blood cells are urged under the centrifugal forces to the outside of the gap 70. The rotor is relatively large in diameter, e.g. 4 to 5 inches, so that adequate centrifugal force can be generated at low rpm for this separation to occur by the time the deflector plate 58 is reached. With a rotor radius of 2.5 inch, at 2000 rpm there is a maximum of approximately 300 g for cell separation. The residence time in the centrifugation gap is adequate for centrifugal separation of the desired constituents.

Figure 3:
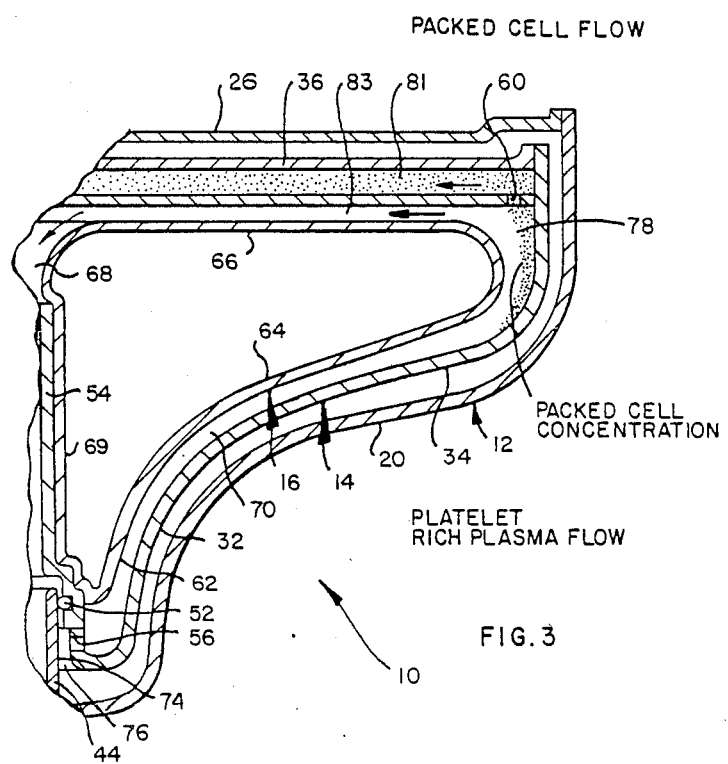
FIG. 3 is a fragmentary view of a portion of the separator of FIGS. 1 and 2.

As shown more clearly in FIG. 3, when the whole blood being separated in the centrifugation gap 70 reaches the upper and outermost portion or corner of the separator volume, at 78, extraction of packed cells takes place. At this region the more dense packed cells are quite precisely separated from the less dense plasma and platelets which are adjacent the inner wall of the centrifugation gap 70. Thus the packed cells pass through the circumferential ring of apertures 60 in the deflector plate 58 into the passage 81 between the deflector plate 58 and the rotor cap 36. The inlet flow pressure is adequate to urge the packed cells toward the center-of the separator until they reach and pass through the upper central conduit 40, pivot pin 42 and the upper outlet port 30. From the outlet port 30 the packed cells are pumped out of the separator by suitable pump means (not shown) or collected in a drainage bag by gravity feed.

The platelet rich plasma (plasma and platelets) at the core 16 wall passes inwardly through the passage 83 between the top 66 of the core and the deflector plate 58 of the rotor into the central reentrant conduit 68 within the rotor core under the feed pressure. Again, the inlet flow pressure is used to overcome centrifugal force in this region, although an outlet pump (not shown) can be used to assist. The continuous flow, here aided by gravity, moves the plasma and platelets downwardly through the interior of the central tubular portion 54, pivot pin 44, and the lower outlet port 24. The platelet rich plasma is then collected in an attached receptacle or pumped out of the separator by suitable means (not shown).

The diameter of the ring of blood inlet apertures 56 on the rotor is kept small to enable a greater differential between the minimum and maximum centrifuging radii. The ratio of platelet rich plasma (PRP) to packed cells removed can be controlled somewhat by using pumps to extract one or the other outlet flows at specific rates.

An important feature of the cell separator of the invention is that the whole blood moved upwardly in the centrifugation gap 70 in the rotor with dynamic force and for a sufficient time to achieve separation before it reaches the top of the gap 70. At the upper and outer region 78 there is adequate gradation between the less dense platelet rich plasma portion and the denser packed cell portion, to effect the needed separation. The construction of the cell separator permits separation of the light density material from the heavy density material by a gentle spinning of the rotor at relatively low speeds, egg. 2000 rpm, as compared to the speed of rotation between 4000 and 5000 rpm of conventional cell separators.

The rotor, core and outer housing or shell of the cell separator all can be formed of plastic and the whole device is disposable after a single use. Hence, the centrifugal separator device of the invention is of simple and economic construction.

The device of the present invention is particularly applicable to the separation of the components of blood. The chief advantage in this respect is that an effective separation of blood components can be obtained using a biologically closed system, as contrasted to currently employed open seal systems which are expensive. By "biologically closed" is generally meant, as with the FDA requirements, that leakage through a gap between relatively moving parts is always internal to the system. Such leakage can therefore only result in mixture of different constituents (such as plasma and packed cells) of the whole blood itself. Exterior access is only possible at fixed ports providing inlet and outlet flows and these are much more assuredly sealed. While the device of the invention is of particular applicability for the separation of the packed cell portion from the platelet rich plasma portion of whole blood, it can also be employed for extracting other concentrates having medical interest, including granulocytes, lymphocytes and neocytes, and can likewise have application for cell washing and autotransfusion.

Figure 4:
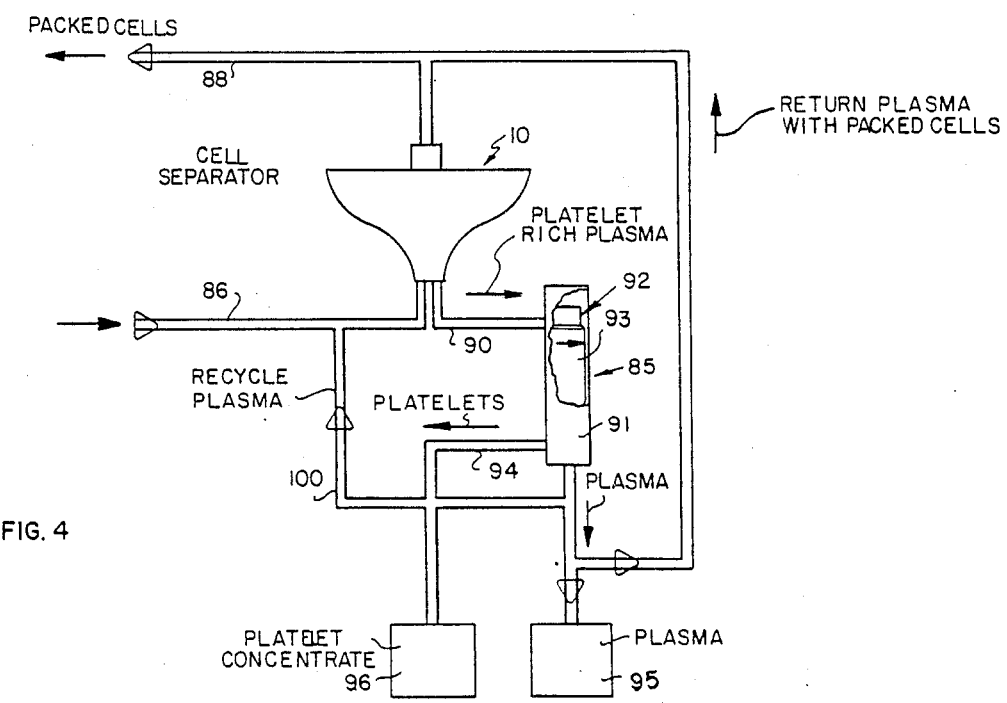
FIG. 4 is a block diagram representation of a disposable system for extraction of platelets from whole blood.

FIG. 4 illustrates another feature of the invention showing a disposable system which can harvest platelet concentrate, pure plasma and packed cells. In this aspect of the invention a separator 10 as illustrated in FIGS. 1 to 3 and described above is employed in conjunction with a membrane filtration unit 85 to provide continuous extraction of packed cells and plasma for return to a donor, while platelet concentrate alone is separately collected.

In this system while blood at 86 is fed to the cell separator 10, the packed cell output from the cell separator 10 is returned to the donor by a conduit 88 and the platelet rich plasma concentrate output from the cell separator is fed via tubing 90 to the membrane filtration device 85.

The membrane filtration device has an interior spinner 92 within a stationary housing 91 and the outer wall of the spinner or the inner wall of the housing has a membrane 93 covering a surface thereof and an internal conduit system (not shown in detail) for collecting plasma passing through the membrane. In operation, the rotating action of the spinner keep the input fluid sweeping the surface of the membrane, causing plasma to be transported through the membrane and into an outlet orifice 90. The plasma output at 90 can be harvested in a separate container at 95 and the platelet concentrate at 94 exiting the membrane filtration device can be collected in a container at 96.

If desired, the plasma at 90 can be returned at line 98 and through the packed cell return line at 88, to the donor. Optionally, also, a fraction of the plasma can be introduced via line 100 with the whole blood feed at 86 to the cell separator 10, to help elutriate the platelets from the blood in the cell separator.

The membrane filtration unit at 85 in FIG. 4 is described and claimed in the application entitled "Method and Apparatus For Separation Of Matter From Suspension," Ser. No. 591,925, filed Mar. 21, 1984, by the present inventor, which is now abandoned and suspended by file wrapper continuation application Ser.

No. 073,378 filed July 13, 1987, and is incorporated herein by reference.

Figure 5:
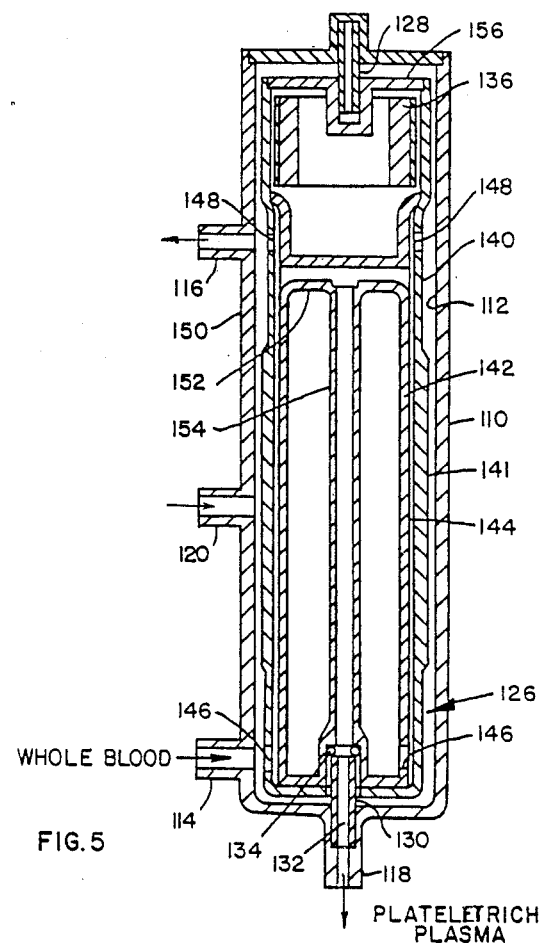
FIG. 5 is a side sectional view of a different system for centrifugal separation of blood constituents.
Figure 7:
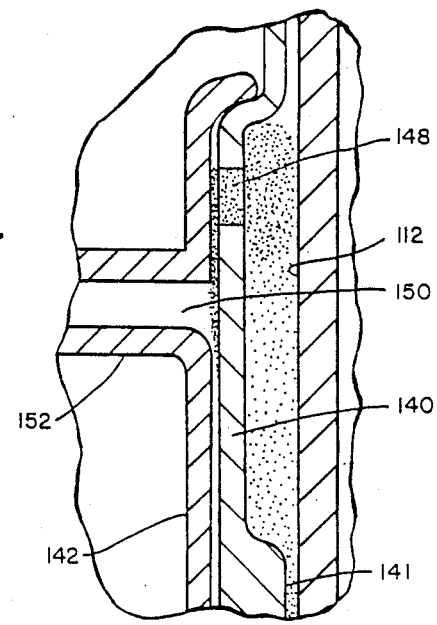
FIG. 7 is an enlarged fragmentary sectional view of a portion of the system of FIGS. 5 and 6, showing the manner in which separation occurs.
Figure 6:
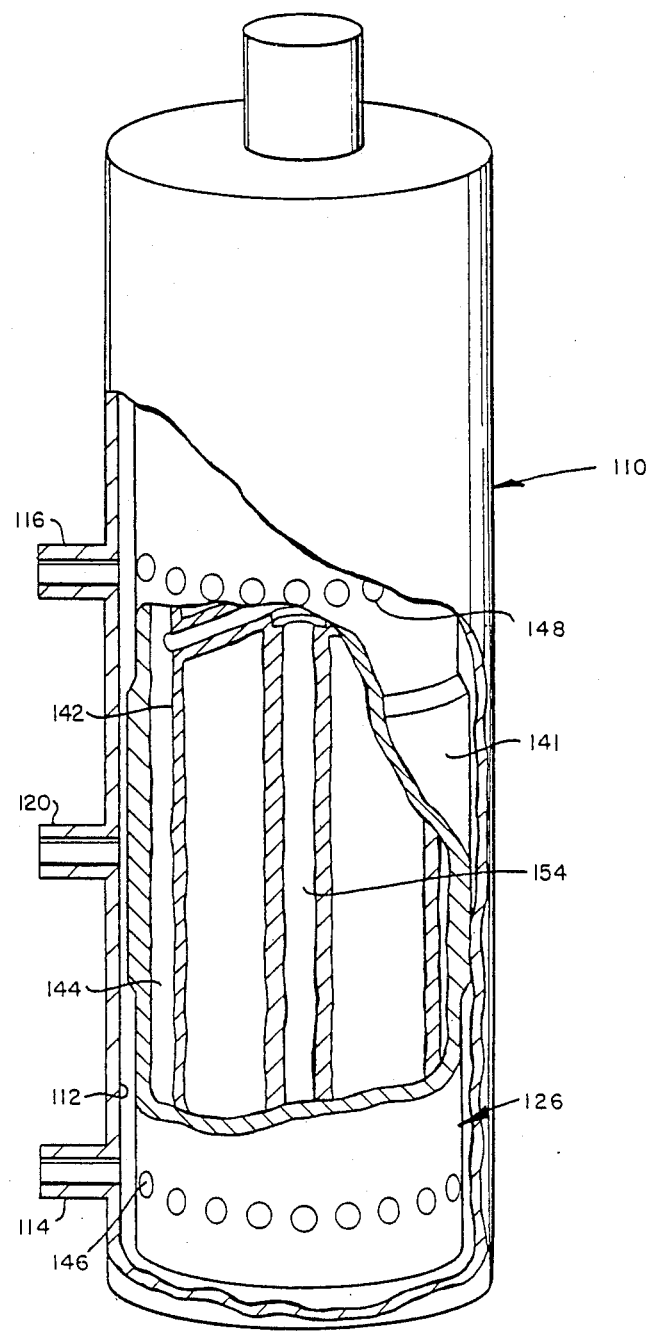
FIG. 6 is a perspective view, partially broken away, of the system of FIG. 5.

FIGS. 5, 6 and 7 depict various aspects of a different biologically closed system for separating lighter and heavier constituents from an input blood flow, this configuration being of even lower cost and more compact form. Referring now to FIGS. 5-7, the housing 110 for the system is configured generally as a right circular cylinder having a substantially right circular inner wall 112, a fixed inlet port 114 for blood input, e.g. whole blood, and a fixed outlet port 116 for outlet of heavier fractions, adjacent the upper end thereof. At the bottom of he housing 110 a fixed outlet port 118 for lighter blood fractions is disposed concentric with the central axis of the system. In the mid region along the vertical length of the housing 110, one or more fixed inlet ports 120 for a biologically compatible fluid, such as plasma or saline solution, is disposed at one or more points about the periphery.

Within the housing 110 a double walled rotor 126 is concentrically disposed about the central axis, and rotatably mounted in fixed upper and lower bearings 128, 130 respectively. The lower bearing 130 has a central orifice 132 in communication with the central outlet port 118 at the lower end of the housing, an internal rotary seal being provided by an 0-ring 144 about the bearing 130. At the upper end of the rotor 126, a magnetic element 136 is mounted so as to be externally driven by magnetic coupling from an external magnetic drive (not shown in detail inasmuch as it may be the same as shown in the example of FIGS. 1-3). Other types of remote drives that do not require mechanical connection through the housing may also be used, although it is preferred to employ the magnetic drive inasmuch as the intention is to provide a low cost disposable. However, where other considerations prevail, a completely different configuration could be used while still providing a biologically closed system, as for example a completely self-contained battery driven motor or a motor with a power source that can be externally energized. In other instances, where continuous separation is desired but the system need not be biologically closed, an external drive directly coupled to the rotor can be used.

The outer wall 140 of the double wall rotor 126 comprises a modified right circular cylinder, having a gap of approximately 0.035" from the upper and lower portions of the inner wall 112 of the housing 110. However the outer wall includes an outwardly extending band 141 in its mid region that is spaced only about 0.010" from the inner housing wall 112. The rotor inner wall 142 is concentric with the opposed base of the outer wall 140 and provides a centrifugation gap 144 of approximately 0.010" to 0.075", here about 0.050". Inlet apertures 146 about the lower region of the outer rotor wall provide an inlet path for input blood into the centrifugation gap region, while in the upper end of the outer wall 140 outlet apertures 148 about the periphery are in communication with the outlet port 116 for the heavier fraction of the fractionated blood. At the upper end of the rotor 126 a horizontal space defines a radially inward passageway 150 between the upper end 152 of the inner wall, which merges into a central passageway 154 extending along the central axis downwardly into communication with the central orifice 132 in the lower bearing 130, thus to define the internal core within the rotor 126. The horizontal upper end wall 156 of the outer wall 140 in this example merely serves as a closure for the internal passageways, and as a mechanical support for the magnetic element 136 and upper bearing 128.

In the system of FIGS. 5-7, the rotor is driven at a suitable rotational velocity, e.g. 2000 rpm, and has a length, such as 4", adequate to provide a residence time within the centrifugation gap sufficient to provide an adequate degree of continuous separation. To this end, whole blood or blood constituents containing both the heavier and lighter fraction passes through the inlet port to within the housing 110. The input blood flow attempts to move continuously upwardly toward the outwardly projecting band 141 on the outer wall 140 of the rotor 126, and through the inlet apertures 146 into the centrifugation gap 144. The restricted gap between the stationary housing inner wall 112 and the band 141 on the rotor 126 and the additional infusion of a compatible fluid introduce a substantial back pressure in this region. Thus the preferential path for the inlet blood is within the centrifugation gap 144. As is evident to those skilled in the art, plasma derived in a process such as that depicted and described in conjunction with FIG. 4 may be used continuously as the compatible fluid input to the mid-region ports 120. Plasma input in the mid region need not be high and the only effect is a slight reduction in the hematocrit of the packed cells provided from the outlet port 116.

Within the centrifugation gap 144, the upwardly ascending blood flow, under centrifugal force, becomes increasingly radially separated into different fractions. The heaver fraction concentrates at the outer wall 140, and at the uppermost region of the length of centrifugation gap 144, heavier matter only is present at the outlet apertures 148. The lighter fraction, specifically platelet rich plasma in the whole blood example, continuously moves inwardly along the radial passageway 150 toward the central axis. Selection of the total aperture area for the outlet apertures 148 relative to the input flow rate enables a continuous balancing of the flows, and therefore continuous separation. The heavier fraction, such as cellular matter, combined with a small amount of bypass whole blood and plasma traverses the outer passageway across the outwardly projecting surface 141. This flow is available for return to the donor, while the platelet rich plasma moves through the central passageway downwardly through the central orifice 132 and the lower bearing 130 and out the central outlet port 118 at the bottom of the housing 110.

The arrangement shown in FIGS. 5-7 is particularly suitable for low cost, high volume applications. Unlike the usual centrifugation technique, it achieves high centrifugation efficiency by establishing a relatively thin flow path in which the radial mass that must be separated is small, so that cells can quickly migrate to the outside under relatively low radial velocities. The upwardly ascending flow is at a sufficiently slow rate for the flow to be essentially laminar, so that the centrifugation effects are not counteracted by turbulence, and a uniform outer layer of heavy matter is made available at the outlet apertures in the rotor wall while the lighter fraction moves inwardly. Consequently, radial ejection of the heavier fraction is automatic and smooth and the various geometries used in the prior centrifuge art, such as probes or separator edges, need not be employed to divide the fractions.

The system of FIG. 8 comprises an implementation of the device of FIGS. 5-7, in which plasma and platelets are separated from whole blood taken from a donor (not shown) with the remaining fraction being returned to the donor. A two needle system is used, a collection needle 160 and an input blood pump 162 feeding the blood input port 164 of a separator device 166 as described in conjunction with FIGS. 5-7. Anticoagulant from a source 170 is also added to the input blood at a controlled rate by an anticoagulant pump 172 (which along with the other pumps is depicted schematically as a conventional peristaltic device). The outlet port 174 for platelet rich plasma from the separator 166 feeds an input 176 of a platelet separator 178 of the rotating spinner type, as previously described, via a pump 180, with the plasma filtrate being collected in a bag or reservoir 182 and also a portion being shunted to an input port 183 in the mid region of the separator 166. The branched flow may be controlled by a valve or adjustable restrictor (not shown) if desired, but positive pressure is maintained by a plasma return pump 184. Platelet concentrate from the platelet separator 178 is fed from the outlet port 186 for non-filtered remainder, as by gravity feed or a pump (not shown) to a second collection bag 188.

As the separator 166 for platelet rich plasma functions, the packed cell output from the remaining outlet port 190 is fed by a return pump 192 to a return needle 194 at the donor, or, alternatively, to a third collection bag 196. Continuous operation in this manner assures maintenance of the desired back pressure in the mid region of the separator 166, but it will also be understood that plasma 182 can be pumped from the plasma reservoir 182 itself if intermittent operation (e.g. a single needle system) is used.

The system of FIG. 8 is again a biologically closed, low cost, disposable system. The two separators 166, 178, three collection bags 182, 188, and 196, together with interconnecting flexible conduit, are all coupled together at static joinders only. Flow rates can be matched, as shown, for continuous operation but buffer reservoirs could be used as well.

From the foregoing, it is apparent that the present invention provides a method and system which is effective for the separation of blood components employing a closed completely disposable system, as contrasted to currently employed open seal systems which are expensive.

Since various changes and modifications of the invention will occur to and can be made readily by those skilled in the art without departing from the invention concept, the invention is not to be taken as limited except by the scope of the appended claims.

What is claimed is:

1. A centrifugal separator system for extracting lighter matter from a liquid suspension comprising:
   a housing having and including an inlet port to receive the liquid suspension, a heavier matter outlet port axially spaced from the inlet port and a lighter outlet port;
   a rotatable interior double shell rotor disposed within said housing for rotation about the axis, said rotor including an outer shell and an inner shell and a centrifugation gap between said inner and outer shells, said rotor being spaced from said housing by a flow gap and including means in said outer shell for providing communication between the centrifugation gap and said inlet port and said heavier matter outlet port;
   means within said double shell rotor communicating with said centrifugation gap and said lighter matter outlet port for conducting the lighter matter from the centrifugation gap to said lighter matter outlet port;
   means within said housing, coupled to said rotor, for rotating said rotor within said housing; and
   wherein the flow of liquid suspension is relatively unrestricted in the centrifugation gap in comparison to the flow gap.

2. A system in accordance with claim 1, wherein said rotating means coupled to said rotor means is adapted for rotating said rotor without mechanical connection thereto, from outside said housing.

3. A system in accordance with claim 1, wherein said housing is a biologically closed cell.

4. A system in accordance with claim 1, wherein the lighter matter can be expressed out of said lighter matter outlet port and the remainder of the liquid suspension can be expressed out of said heavier matter outlet port during rotation of said rotor means.

5. A system in accordance with claim 1, wherein said centrifugal separator is a continuous flow separator in which liquid suspension can be introduced into said housing through said inlet port, in which the lighter matter can be expressed out of said housing through said lighter matter outlet port, and in which the remainder of the liquid suspension can be expressed out of said housing through said heavier matter outlet port, all during rotation of said rotor means.

6. A system in accordance with claim 5, wherein said housing is a biologically closed cell.

7. A system according to claim 1
   wherein said housing axis is a central axis, and
   wherein said double shell rotor is rotatable concentrically about said central axis.

8. A continuous flow centrifugal separator comprising:
   a fixed housing disposed about an axis and having an inlet port, an outlet port for heavier matter that is axially spaced from the inlet port and an outlet port for lighter matter; and
   a rotor disposed within the housing for rotation about the axis, the rotor having an outer shell and an inner wall spaced radially inward from the outer shell to define therebetween a gap which extends axially between the housing inlet port and the housing heavier matter outlet port, the outer shall having at least one shell inlet port therein to provide communication of fluid from the housing inlet port into the gap, at least one shell heavier material outlet axially spaced from the shell inlet port in a direction toward the housing heavier material outlet port to provide communication from the gap to the housing heavier material outlet port, the rotor including a communication path for lighter material that extends from the gap and radially inwardly from the shell heavier material outlet port to the shell lighter material output port.

9. The centrifugal separator according to claim 8
   wherein said housing axis is a central axis, and
   wherein said rotor is rotatable concentrically about said central axis.

10. A centrifugal separator according to claim 9, wherein the housing lighter material outlet port is concentric with the central axis.

11. A centrifugal separator according to claim 8, wherein the housing provides a biologically closed container.

12. A centrifugal separator according to claim 8, wherein a gap is defined between the rotor and the housing and at least a portion of the gap between the rotor and housing is no greater than the centrifugation gap.

13. A centrifugal separator according to claim 8, wherein at least a portion of the gap between the rotor and the housing is smaller than the centrifugation gap.

14. A centrifugal separator according to claim 8, wherein the centrifugation gap provides a flow path between the at least one shell inlet port and the at least one shell outlet port which is preferential to flow therebetween through a gap defined between the housing and the rotor.

* * * * *